United States Patent [19]

Van Doorn et al.

[11] Patent Number: 5,118,854

[45] Date of Patent: Jun. 2, 1992

[54] PREPARATION OF ORTHO SUBSTITUTED DIPHENYLPHOSPHIDES

[75] Inventors: Johannes A. Van Doorn; Nicolaas Meijboom; Richard L. Wife, all of Amsterdam, Netherlands

[73] Assignee: Shell Oil Company, Houston, Tex.

[21] Appl. No.: 771,888

[22] Filed: Oct. 7, 1991

Related U.S. Application Data

[63] Continuation of Ser. No. 175,021, Mar. 30, 1988, abandoned.

[30] Foreign Application Priority Data

Apr. 8, 1987 [NL] Netherlands ............... 8700822

[51] Int. Cl.⁵ ............................................ C07F 9/28
[52] U.S. Cl. ........................................................ 568/13
[58] Field of Search .............................. 568/8, 13, 17

[56] References Cited

U.S. PATENT DOCUMENTS 2,437,795  3/1948  Walling ................................ 568/8
4,393,240  7/1983  Stille .................................... 568/13

FOREIGN PATENT DOCUMENTS

87/240  2/1976  Austria .

OTHER PUBLICATIONS

J. Org. Chem. 1985; 50 pp. 4329–4332.
Chemical Abst. vol. 103, 1985 87982P.
Chemical Abst. vol. 103, 1985 178342W.
Brown et al., Tetrahedron Letters, vol. 21, pp. 581–584 (1980).

*Primary Examiner*—Wayne Langel
*Assistant Examiner*—Stuart L. Hendricks

[57] ABSTRACT

Alkali metal di(2-alkoxyphenyl)phosphide is produced in good yield by reaction of alkali metal and the corresponding tri(2-alkoxyphenyl)-phosphine in liquid ammonia.

14 Claims, No Drawings

PREPARATION OF ORTHO SUBSTITUTED DIPHENYLPHOSPHIDES

This is a continuation of U.S. application Ser. No. 07/175,021, filed Mar. 30, 1988 abandonded.

FIELD OF THE INVENTION

This invention relates to the production of alkali metal di(2-alkoxyphenyl)phosphide by reaction of alkali metal and the corresponding tri(2-alkoxyphenyl)phosphine.

BACKGROUND OF THE INVENTION

The production of arylphosphines can be complicated if the substituents on the phosphorus are not identical. In situations where production of mixed alkyl-aryl phosphines is desired, the synthesis generally involves the use of at least one type of organo alkali metal intermediate, the synthesis of which is often difficult or inefficient.

One class of bidentate phosphorus ligands which are mixed alkyl-aryl phosphines has become of interest as precursor composition useful in the production of a type of polymeric material known as polyketones. These polyketones are linear alternating copolymers of carbon monoxide and at least one ethylenically unsaturated hydrocarbon. Polymerization takes place in the presence of a catalyst composition formed from a compound of palladium, cobalt or nickel, an anion of certain strong non-hydrohalogenic acids and the bidentate ligand. Such bidentate phosphorus ligands are illustrated by the formula

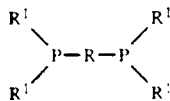

wherein $R^1$ independently is an aryl substituent and R is a divalent bridging group, often trimethylene. The processes for production of the polyketones are illustrated by published European Patent Applications 0,121,965 and 0,181,014. Good results are obtained employing ligands in which each $R^1$ is phenyl, an illustrative ligand therefore being 1,3-bis(diphenylphosphino)propane. One of the least complicated methods of producing this ligand involves the reaction of an alkali metal di($R^1$)-phosphide, e.g., sodium diphenylphosphide, with an α,Ω-dihaloalkane such as 1,3-dichloropropane. Corresponding methods produce other bis(diarylphosphino)alkanes.

Recent process developments in polyketone production have shown that particularly good results are on occasion obtained if the bidentate phosphine ligand has at least one and preferably each of the aryl groups substituted in the ortho position with an alkoxy group. Such ligands are represented by the above formula wherein each $R^1$ is 2-alkoxyphenyl. Accordingly, a process for the production of alkali metal di(2-alkoxyphenyl)phosphide would be of advantage.

Production of alkali metal diphenylphosphide by reaction of triphenylphosphine with alkali metal in liquid ammonia is well known. Similar processes to make substituted-phenyl alkali metal phosphides from the corresponding phosphine are satisfactory in some instances and in some instances are not, depending in part on the substituent desired and upon the location on the aromatic ring where the substituent is located. Such a process works well, for example, in the production of alkali metal di(4-methylphenyl)phosphides from the corresponding substituted triphenylphosphines but is not entirely satisfactory for the production of alkali metal di(2-methylphenyl)phosphide.

A production of potassium di(2-methoxyphenyl)-phosphide by reaction of potassium and tri(2-methoxyphenyl)phosphine in dioxane at 20° C. is disclosed by Brown et al, Tetrahedron Letters, Vol. 21, pp. 581–584 (1980). The phosphide is formed and subsequently reacted in situ and no conversion of the phosphine to phosphide is specified or was determined.

SUMMARY OF THE INVENTION

This invention relates to an improved process for the production of certain alkali metal di(substituted phenyl)phosphides from the corresponding tri(substituted phenyl)phosphine. More particularly, it relates to a process for the production of an alkali metal di(2-alkoxyphenyl)phosphide by reaction of alkali metal and the corresponding tri(2-alkoxyphenyl)phosphine.

DESCRIPTION OF THE INVENTION

The process of the invention comprises the reaction of alkali metal and tri(2-alkoxyphenyl)phosphine in liquid ammonia. Suitable alkali metals are the members of Group IA of the Periodic Table of Elements, i.e., lithium, sodium, potassium, rubidium and cesium. In part because of reasons of economy, the lower alkali metals lithium, sodium and potassium are preferred and best results are obtained when sodium is employed.

The tri(2-alkoxyphenyl)phosphines of the invention are substituted triphenylphosphines wherein each phenyl group is substituted in an ortho position with an alkoxy group of up to 10 carbon atoms, preferably of up to 4 carbon atoms. Suitable tri(2-alkoxyphenyl)phosphines are represented by the formula

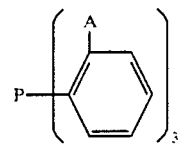

wherein A is alkoxy as defined above. Illustrative of A groups are methoxy, ethoxy, propoxy, i-propoxy, sec-butoxy, t-butoxy, hexoxy, octoxy and decoxy. Best results are obtained if the alkyl moiety is a straight chain primary alkyl group and particularly preferred as the A group is methoxy.

The reactants are contacted in liquid ammonia. Because ammonia normally boils at about −33° C., the reaction mixture must be cooled or in the alternative the reaction is conducted under elevated pressure. Although reaction pressures up to about 4 atmospheres are satisfactory, preferred reaction conditions employ a pressure of substantially one atmosphere and a reaction temperature at which the ammonia is maintained in the liquid phase. Such temperatures are suitably from about −35° C. to about −100° C. but preferably are from about −35° C. to about −80° C. A suitable ratio of alkali metal to triphosphine will vary and is typically from about 1 gram atom to about 3 gram atoms of alkali metal per mol of triphosphine. Best results are obtained when about 2 gram atoms of alkali metal are employed per mol of triphosphine. The quantity of ammonia to be employed is sufficient to maintain the reactants and products in solution. Typical amounts are from about 1 liter to about 125 liters of liquid ammonia per gram atom of alkali metal, more typically from about 10 liters to about 40 liters of liquid ammonia per gram atom of alkali metal.

On occasion it has been found useful to add a quantity of an ether to the reaction mixture to enhance the yield of di(2-alkoxyphenyl)phosphide. Suitable ethers are the commonly available ethers of from 2 to 10 carbon atoms and are hydrocarbyl except for the presence of from 1 to 2 ether oxygen atoms. Illustrative ethers are dialkyl ethers such as dimethyl ether, diethyl ether and methyl isopropyl ether and cyclic ethers such as tetrahydrofuran and dioxane. Tetrahydrofuran is a preferred ether to be employed in modifications where ether is added. No ether is required for the process of the invention but when ether is added it is added in quantities of up to about 0.75 liter per liter of liquid ammonia. Quantities of ether from about 0.05 to about 0.5 liter per liter of liquid ammonia are preferred when an ether is present.

The reactants are contacted in conventional reactors where pressure and/or cooling may be employed and reactant contact maintained as by shaking or stirring. No special equipment is required beyond that usually employed in reactions of very active materials such as alkali metals. Subsequent to reaction, an acidic material is often added to consume any unreacted alkali metal and the ammonia removed as by evaporation. The product mixture contains the desired alkali metal di(2-alkoxyphenyl)phosphide product as well as byproducts such as 2-alkoxyphenyl alkali metal. The product mixture is separated as by a selective extraction but more conventionally is used as such without interference by the byproducts. Alternatively, the initial product mixture is used in a subsequent reaction without the necessity of removing the ammonia.

The production of alkali metal di(2-alkoxyphenyl)-phosphides by the process of the invention is similar to a known process but the process is applied to a particular class of phosphine reactants, i.e., the tri(2-alkoxyphenyl)phosphines. Although the conventional alkali metal reaction works well with tri(4-methylphenyl)-phosphine it does not in the case of tri(2-methylphenyl)-phosphine, perhaps because of steric hindrance around the phosphorus atom. However, in the case of the alkoxyphenylphosphines, the tri(2-alkoxyphenyl)phosphines give excellent conversions to alkali metal di(2-alkoxyphenyl)phosphides whereas unsatisfactory conversions are obtained with reaction of tri(4-alkoxyphenyl)phosphines. The tri(3-substituted phenyl)phosphines also give satisfactory conversions in both cases, but the phosphide products are not thought to have the desirable uses of the alkali metal di(2-alkoxyphenyl)-phosphides.

The alkali metal di(2-alkoxyphenyl)phosphide product of the process of the invention is reacted by conventional procedures with, for example, 1,3-dibromopropane to give a good yield of 1,3-bis[di(2-alkoxyphenyl)-phosphino]propane, for example, 1,3-bis[di(2-methoxyphenyl)phosphino]propane. Such diphosphines are useful as catalyst composition precursors in the production of polyketone polymers as shown, for example, in copending U.S. application Ser. No. 099,263, filed Sep. 21, 1987.

The invention is further illustrated by the following Comparative Examples (not of the invention) and Illustrative Embodiments, which should not be construed as limiting.

COMPARATIVE EXAMPLE I

Sodium diphenylphosphide was produced by the following procedure. To 100 ml of liquid ammonia in a mechanically stirred reaction vessel maintained at −78° C. with cooling were successively added 8 mmol of sodium and 4 mmol of triphenylphosphine. After 4 hours, 4 mmol of ammonium chloride was added and after 15 minutes the ammonia was removed by evaporation. Analysis of the residue showed that the triphenylphosphine had been quantitatively converted to sodium diphenylphosphide.

COMPARATIVE EXAMPLE II

Di(methylphenyl)phosphides were produced according to the procedure of Comparative Example I except that the corresponding tri(methylphenyl)phosphines were employed in place of the triphenylphosphine. The results obtained with the three methyl-substituted phosphines are shown in Table I.

TABLE 1

| Location of methyl substituent | Conversion to sodium di(methylphenyl)phosphide |
|---|---|
| ortho | 55% |
| meta | 84% |
| para | 79% |

COMPARATIVE EXAMPLE III

Sodium di(4-methoxyphenyl)phosphide was produced by the procedure of Comparative Example I except that tri(4-methoxyphenyl)phosphine was used instead of triphenylphosphine. The conversion of the phosphine to the phosphide was 2%.

ILLUSTRATIVE EMBODIMENT I

Sodium di(2-methoxyphenyl)phosphide was produced by the procedure of Comparative Experiment I except that tri(2-methoxyphenyl)phosphine was employed in place of the triphenylphosphine. The conversion of the phosphine to phosphide was 88%.

ILLUSTRATIVE EMBODIMENT II

Sodium di(2-methoxyphenyl)phosphide was produced by substantially the same procedure as Illustrative Embodiment I, except that the reaction temperature was −40° C. instead of −78° C. and the addition of ammonium chloride was effected after 1 hour instead of after 6 hours. The tri(2-methoxyphenyl)phosphine was found to have been quantitatively converted into sodium di(2-methoxyphenyl)phosphide.

COMPARATIVE EXAMPLE IV

Sodium di(3-methoxyphenyl)phosphide was produced by the procedure of Comparative Example I except that tri(3-methoxyphenyl)phosphine was employed in place of the triphenylphosphine. The conversion of the phosphine to the phosphide was 76%.

What is claimed is:

1. The process of producing alkali metal di(2-alkoxyphenyl)phosphide by reacting alkali metal and tri(2-alkoxyphenyl)phosphine in liquid ammonia.

2. The process of claim 1 wherein the alkali metal is lithium, sodium or potassium.

3. The process of claim 2 wherein the tri(2-alkoxyphenyl)phosphine is represented by the formula

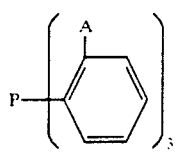

wherein A is alkoxy of up to 10 carbon atoms.

4. The process of claim 3 wherein A is primary, straight-chain alkoxy of up to 4 carbon atoms.

5. The process of claim 3 wherein the alkali metal is sodium.

6. The process of claim 5 wherein A is methoxy.

7. A process for producing alkali metal di(2-alkoxyphenyl)phosphide by reacting alkali metal and tri(2-alkoxyphenyl)phosphine in liquid ammonia and in the additional presence of between about 0.05 and about 0.5 liter of an ether per liter of liquid ammonia.

8. The process of claim 7 wherein said ether is selected from dialkyl ethers or cyclic ethers.

9. The process of claim 8 wherein said ether is a cyclic ether.

10. The process of claim 9 wherein said cyclic ether is tetrahydrofuran.

11. The process of claim 8 wherein said tri(2-alkoxyphenyl)phosphine is tri(2-methoxyphenyl)phosphine and said alkali metal di(2-alkoxyphenyl)phosphide is an alkali metal di(2-methoxyphenyl)phosphide.

12. The process of claim 11 wherein said alkali metal is sodium.

13. The process of claim 1 wherein said tri(2-alkoxyphenyl)phosphine is tri(2-methoxyphenyl)phosphine and said alkali metal di(2-alkoxyphenyl)phosphide is an alkali metal di(2-methoxyphenyl)phosphide.

14. The process of claim 1 wherein said alkali metal and said tri(2-alkoxyphenyl)phosphine are reacted at a pressure of about one atmosphere and a temperature of about $-35°$ C. to about $-100°$ C.

* * * * *